(12) United States Patent  
Millgård

(10) Patent No.: US 9,284,065 B2  
(45) Date of Patent: Mar. 15, 2016

(54) AIRCRAFT DOCKING SYSTEM

(75) Inventor: Lars Millgård, Undersåker (SE)

(73) Assignee: Safegate International Aktiebolag, Malmö (SE)

( * ) Notice: Subject to any disclaimer, the term of this patent is extended or adjusted under 35 U.S.C. 154(b) by 2327 days.

(21) Appl. No.: 11/384,829

(22) Filed: Mar. 21, 2006

(65) Prior Publication Data

US 2007/0222969 A1    Sep. 27, 2007

(51) Int. Cl.
- *G01C 3/08* (2006.01)
- *B64F 1/00* (2006.01)
- *G08G 5/00* (2006.01)
- *G08G 5/06* (2006.01)
- *G01N 21/17* (2006.01)

(52) U.S. Cl.
CPC . *B64F 1/002* (2013.01); *G01C 3/08* (2013.01); *G08G 5/0026* (2013.01); *G08G 5/065* (2013.01); *G01N 2021/1795* (2013.01)

(58) Field of Classification Search
CPC .......... B64F 1/002; G01C 3/08; G08G 5/065
USPC ............................................ 356/139.03, 342
See application file for complete search history.

(56) References Cited

U.S. PATENT DOCUMENTS

| | | | |
|---|---|---|---|
| 5,914,776 A * | 6/1999 | Streicher | 356/5.01 |
| 6,100,964 A | 8/2000 | De Cremiers | |
| 6,542,086 B2 | 4/2003 | Baumgartner et al. | |
| 6,563,432 B1 * | 5/2003 | Millg.ang.rd | 340/961 |
| 6,704,098 B2 * | 3/2004 | Anderberg | 356/4.01 |
| 6,722,610 B1 * | 4/2004 | Rawdon et al. | 244/103 W |
| 2003/0076485 A1 * | 4/2003 | Ruff et al. | 356/5.09 |

FOREIGN PATENT DOCUMENTS

| | | |
|---|---|---|
| EP | 1 482 326 | 12/2004 |
| RU | 2093899 C1 | 10/1997 |
| RU | 2119175 C1 | 9/1998 |
| WO | WO 03/104081 | 12/2003 |

OTHER PUBLICATIONS

"Scattering," from Wikipedia (http://en.wikipedia.org/wiki/Scattering), as of 12:31, Nov. 26, 2007; retrieved Dec. 10, 2007.

* cited by examiner

Primary Examiner — Timothy A Brainard
(74) Attorney, Agent, or Firm — Duane Morris LLP

(57) ABSTRACT

An aircraft docking system is configured to be located at a docking site. The system comprises distance determining means configured to determine, using electromagnetic radiation signal reception means, at least a distance between the system and an aircraft. The distance determining means are further configured to measure at least one property of a receiver signal received by the signal reception means, the property being related to the visibility at the docking site, compare said measure of the at least one receiver signal property with a threshold value and, depending on the comparison, provide a signal indicative of whether or not the visibility at the docking site is good enough to allow safe docking of the aircraft.

20 Claims, 4 Drawing Sheets

AIRCRAFT DOCKING SYSTEM

FIELD OF THE INVENTION

The present invention relates to an aircraft docking system located at a docking site, said system comprising distance determining means configured to determine at least a distance between the system and an aircraft.

DESCRIPTION OF RELATED ART

In recent years demand at airports for efficient operation has increased and with that has arisen at many airports a need to replace manual marshalling of aircraft to the gate by automatic aircraft docking systems.

Automatic docking systems are typically based on techniques, which are more or less affected by reduced visibility, e.g. due to fog and precipitation. The expression "visibility" is to be interpreted as atmospheric transmittance of electromagnetic radiation at a relevant wave-length. One example of such a system is disclosed in U.S. Pat. No. 6,563,432 in which a system for detecting and determining a distance to aircraft scans an area at a gate with laser pulses. The reflected laser pulses are analyzed in order to detect solid objects and also to distinguish between solid objects and fog or precipitation.

Another example of an automatic docking system, which is affected by visibility conditions, is disclosed in U.S. Pat. No. 6,542,086. The system in U.S. Pat. No. 6,542,086 utilizes a video camera as a sensor.

A drawback with such systems is that they do not always allow docking in all weather conditions during which the airport is open for traffic. The aircraft may need guidance at a distance of 80-100 meters away from the nearest location where a docking system can be mounted, typically at a gate, while the airport may still be open for traffic at a visibility less than 80-100 meters. A result of this is that, during the conditions when automatic docking is impossible due to fog or precipitation, the dockings has to be carried out manually by marshallers. A problem with such a situation is that the need for manual marshalling may not be apparent until an aircraft is approaching a gate, and it turns out that the fog or precipitation is too dense for the docking system to be able to give guidance. At a large airport this may happen at several gates at the same time and as it is not planned it may cause disturbances of the airport operation with associated problems such as added cost or decreased safety.

While the system disclosed in the U.S. Pat. No. 6,563,432 detects, identifies and docks aircrafts and also determines whether a detected object is solid or whether fog or precipitation is present, it does not determine whether automatic docking is impossible or not.

Generally, measurement of visibility is performed at airports by the use of visibility meters located near to runways. The output of the existing visibility meters is, however, typically not very representative of the conditions at the docking systems as these normally are located at gates in close vicinity of terminal buildings, and as the density of fog usually vary very much over an airport. Moreover, installing such a visibility meter at each gate is not an optimal solution. The output of the meter may still not be representative of the conditions that governs the performance of the docking system as fog often exists in patches and as the operating area for the system is a sector extending about 100 meters out from the system. Another disadvantage with such a solution is the added cost of providing a plurality of expensive visibility meters.

SUMMARY OF THE INVENTION

Hence, from the above discussion of drawbacks related to prior art systems it turns out that a need exists in the art for an aircraft docking system with the ability to determine whether the visibility conditions allow docking with the system or not.

An object of the present invention is therefore how to configure a docking system to determine the visibility conditions within its working area and to provide a signal when these conditions no longer allow docking with the system.

To achieve this object the present invention provides, in a first aspect, an aircraft docking system configured to be located at a docking site. The system comprises distance determining means configured to determine, using electromagnetic radiation signal reception means, at least a distance between the system and an aircraft. The distance determining means are further configured to measure at least one property of a receiver signal received by said signal reception means, said property being related to the visibility at the docking site, compare said measure of the at least one receiver signal property with a threshold value, and depending on said comparison, provide a signal indicative of whether or not the visibility at the docking site is good enough to allow safe docking with the system.

In a second aspect, the invention provides a method for controlling aircraft docking in an aircraft docking system located at a docking site. The system comprises distance determining means configured to determine, using electromagnetic radiation signal reception means, at least a distance between the system and an aircraft and the distance determining means perform the steps of measuring at least one property of a receiver signal received by said signal reception means, said property being related to the visibility at the docking site, comparing said measure of the at least one receiver signal property with a threshold value, and depending on said comparison, providing a signal indicative of whether or not the visibility at the docking site is good enough to allow safe docking with the system.

In a third aspect, the invention provides a computer program comprising software instructions that, when executed in a computer performs a method as discussed above.

In a fourth aspect, the invention provides a use of an aircraft docking system for controlling operations at an airport.

In other words, a system according to the present invention is configured to check the visibility conditions of the working area of the docking system before and/or during docking of an aircraft. The system measures characteristics which are related to the visibility at the docking site and which limits the performance of the system. The measuring results are used as a determining factor in determining whether the visibility conditions allow safe docking or not.

An advantage of the present invention is hence that it provides to an operator of an airport an enhanced ability to determine whether or not it is possible to perform a docking operation when visibility is reduced to such an extent that there exists an uncertainty whether or not safe docking is possible or not. For example, prior art systems are typically unable to distinguish between dense fog or precipitation and parts of approaching aircraft. Needless to say, such lack of distinguishing capability may lead to dangerous situations. On the other hand, prior art systems may be configured to account for such lack of distinguishing ability and simply provide a signal to the effect that docking is impossible when the system is uncertain. This, however, means that the availability of prior art systems is not as high as the availability of a system according to the present invention.

Furthermore, an advantage is that it is possible to determine in real-time, and continuously, whether or not the density of the fog or the precipitation makes automatic docking impossible or not and keep the traffic controllers informed about it. The need for marshalling can be foreseen and thereby marshallers can be in place when the aircraft arrive and disturbances in terms of docking delays can be avoided. Efficient airport operation is thereby achieved, e.g. in terms of less waiting time for aircraft and faster and hence more efficient allocation of arriving aircraft to gates and terminals where automatic docking is possible.

Yet an advantage of the invention is that, by providing a solution to the problems as discussed above, an already existing docking system may be adapted to also provide a signal indicative of the visibility conditions at the docking site. Typically, an implementation will only entail re-programming of control software in the system, which means a large saving in cost when comparing with a situation in which a separate visibility system would be needed. There is no need to adapt any hardware of the existing docking system as the wavelength interval in which a docking system operates is also suitable for operation in connection with the determining of visibility conditions.

Embodiments of the invention include those where the distance determining means are configured to measure receiver signal properties in terms related to scattering of the electromagnetic radiation. For example, the distance determining means may comprise laser ranging means and the distance determining means may then be configured to measure scattering of the laser radiation. Alternatively, the distance determining means may comprise radar ranging means and the distance determining means may then be configured to measure scattering of radar radiation. In further embodiments, backscattered electromagnetic radiation, or more precisely, a power distribution of the backscattered radiation, indicates the scattering.

Further embodiments include those where the distance determining means comprise signal reception means comprising imaging means configured to provide two-dimensional images of the docking site and where the distance determining means are configured to measure the at least one property of the receiver signal at least in terms related to a contrast difference between at least two areas within an image. These image areas may correspond to predetermined locations, preferably at a same distance from the system, at the docking site.

In other words, where the docking system utilizes a two-dimensional imaging technique, the measure of visibility conditions is the contrast in an image. Analysing an image signal used for determining the location of the aircraft and determining the deterioration of this signal caused by the fog or precipitation provides a good indication of whether or not the visibility deterioration exceeds the level above which docking is unsafe or even impossible.

The imaging means may be configured to detect electromagnetic radiation in any of a visual wavelength interval and an infrared wavelength interval as well as detecting electromagnetic radiation in both of these wavelength intervals.

BRIEF DESCRIPTION OF THE DRAWINGS

The invention will now be described in more detail with reference to the attached drawings on which.

PREFERRED EMBODIMENTS

Figure 1:
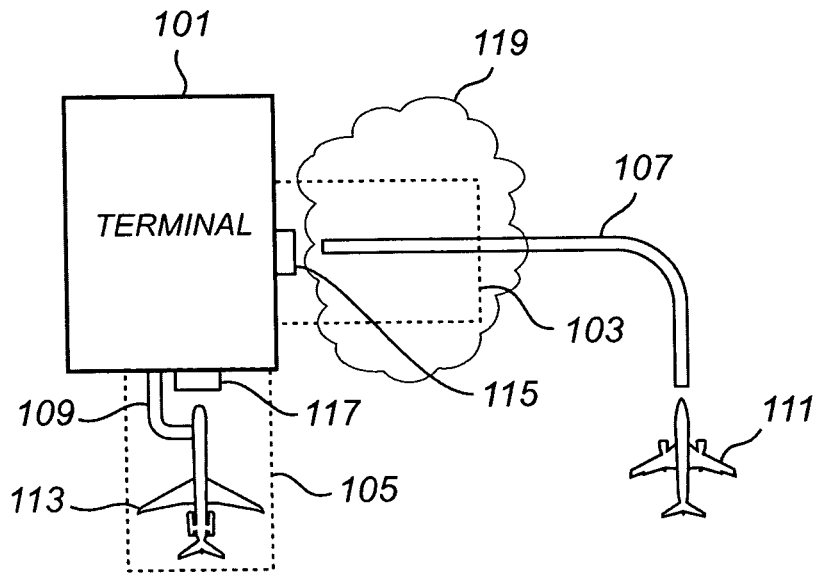
FIG. 1 schematically illustrates docking sites at which docking systems according to the invention are arranged.

FIG. 1 illustrates schematically a view from above of a situation at an airport. A terminal 101, which may be a passenger terminal and/or a freight terminal, is configured with a first aircraft docking system 115 and a second aircraft docking system 117. A first docking site 103 and a second docking site 105 are located at each docking system 115, 117 respectively. Although the docking sites are indicated by dashed lines in FIG. 1, these lines need not represent actual markings on the ground but should only be perceived as an aid in reading the present description.

Moreover, although FIG. 1 shows that both docking systems 115, 117 are attached to the terminal 101, alternative configurations include those where a docking system is not directly attached to a terminal but to any other suitable means at a docking site. In fact, a docking site may not be directly associated with a specific terminal, and may also be associated with a designated docking site anywhere at an airport where airport operations allow docking.

The situation illustrated in FIG. 1 is one in which a first aircraft 111 is approaching the first docking site 103 along a guiding line 107 on the ground. A second aircraft 113 is located at the second docking site 105, having performed a successful docking operation and being connected to the terminal 101 via a passenger bridge 109.

The first docking site 103 is to a large extent covered by fog 119. The fog 119 extends in three spatial dimensions in the atmosphere at the docking site and is to be understood as being a potential obstacle that may prevent safe docking of the first aircraft 111 as it approaches the first docking system 115.

As is known, fog or precipitation affects visibility mainly in that incident electromagnetic radiation is scattered by the droplets in the atmosphere. During the scattering process, the illuminated droplets reemit some fraction of the incident electromagnetic radiation in all directions. The droplets then act as point sources of the reemitted energy. Some portion of the incident electromagnetic radiation is scattered backwards towards the radiation source, dependent on the relation between the droplet size and the radiation wavelength. The relation between visibility and scattered electromagnetic radiation is widely described in the literature, e.g. in "Ground-based remote sensing of visual range/Visual-range lidar", Verein Deutscher Ingenieure VDI 3786, or in "Elastic Lidar: Theory, practise and analysis methods", V. A. Kovalev, W. E. Eichinger, Hoboken, N.J., Wiley, 2004.

For docking systems relying on electromagnetic emission means, e.g for emission of pulses, the scattering reduces the amount of received energy reflected from objects to be detected. For docking systems relying on imaging means, the scattering causes a reduction of contrast in the image used.

Figure 2A:
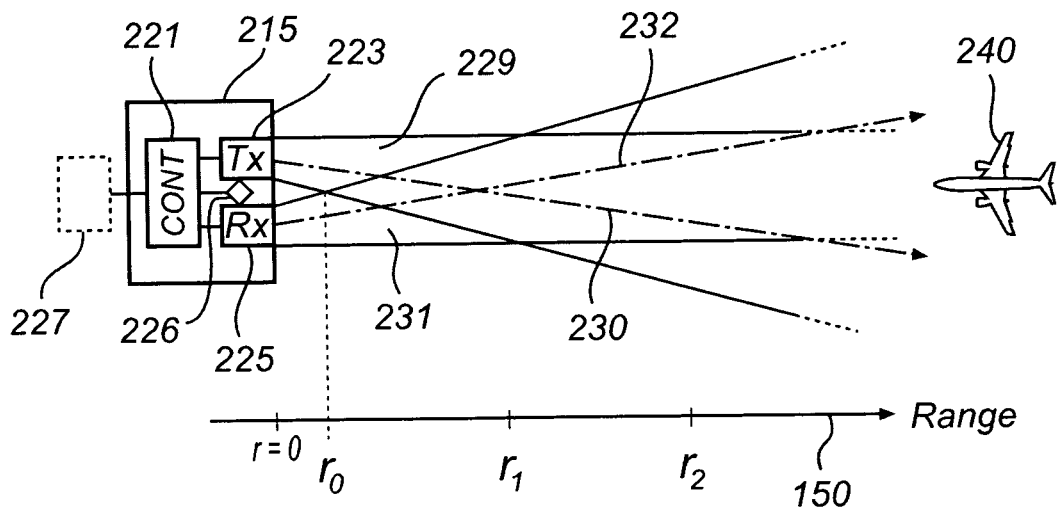
FIG. 2a schematically illustrates a docking system according to a first embodiment of the present invention.
Figure 2B:
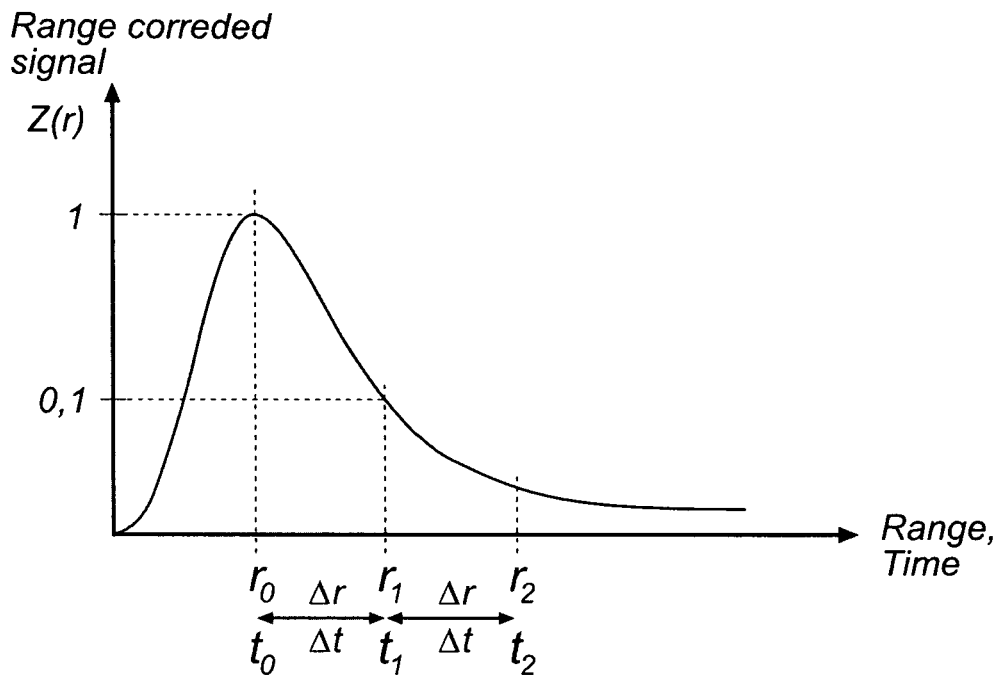
FIG. 2b is a graph of a response curve relating to a electromagnetic pulse reflected in fog.

Turning now to FIGS. 2a and 2b, a docking system 215 will be described, which utilizes electromagnetic radiation in terms of emission of pulses and reception of backscattered radiation of these pulses. The docking system 215 is configured to determine, in real-time, distances to an approaching aircraft 240 and also configured to indicate whether or not visibility at a docking site, located between the docking system 215 and the approaching aircraft 240, is good enough to allow safe docking of the aircraft 240.

The docking system 215 of FIG. 2a, which may represent any of the docking systems 115, 117 discussed above in connection with FIG. 1, comprises a control unit 221, a transmitter 223 and a receiver 225. The transmitter 223 is configured, under the control of the control unit 221, to emit electromagnetic radiation pulses that is in the form of laser radiation (although other embodiments may comprise a transmitter/receiver pair that are configured to operate with radar pulses). The radiation exits from the transmitter in a transmission beam 229 along a transmission beam direction 230, as schematically illustrated in FIG. 2a. Correspondingly, the receiver is configured, also under the control of the control unit 221, to receive backscattered radiation in a reception beam 231 along a reception beam direction 232 and to provide a representative signal of the backscattered radiation to the control unit 221.

The transmitter 223 and the receiver 225 are configured such that they, via a beam direction device 226 controlled by the control unit 221, can be directed in any desired spatial direction. As the skilled person will realize, the beam direction device 226 may be realized in the form of mirrors, stepper motors etc.

The docking system 215 may, as indicated in FIG. 1, form part of a larger system arranged at an airport terminal and also be connected to an external control system 227 operated by airport staff.

Figure 4:
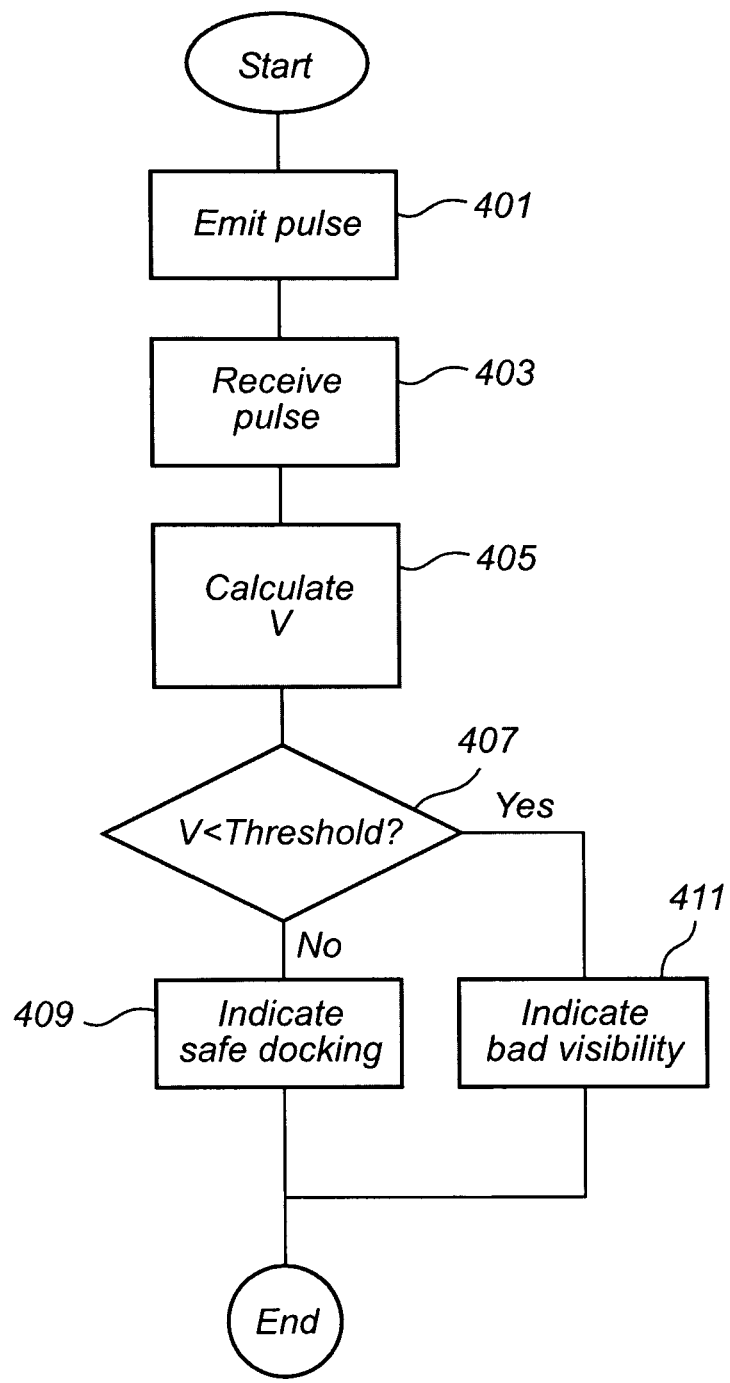
FIGS. 4 and 5 are flow charts of methods according to the invention.

Now follows a description of how the docking system 221 in FIG. 2 operates in order to provide an indication of whether or not safe docking is possible, where the distance determining of the docking system 221 utilizes the transmitter 223 and the receiver 225 to emit and receive electromagnetic pulses in the form of either laser pulses or radar pulses. Reference will be made also to the flow chart in FIG. 4.

The graph in FIG. 2b shows a typical power distribution $Z(r)$ of a range-corrected receiver signal of the system when a pulse has been emitted, in an emission step 401, towards homogenous fog and backscattered radiation has been receive by the receiver 225, in a reception step 403, in the form of a receiver signal having a power distribution $P(r)$. Then follows a calculation step 405 during which a value for visibility V is calculated.

In the calculation step 405, the range-corrected power distribution $Z(r)$ is initially calculated as $Z(r)=r^2*P(r)$ to compensate for the fact that the receiver signal at long distances falls off as $1/r^2$. r is the distance between the transmitter/receiver and the reflecting/scattering object.

The visibility V is then calculated from the range-corrected receiver signal $Z(r)$, e.g. by using an algorithm disclosed in DE 19642967 or by using the so called method of asymptotic approximation. According to this method the visibility V can be calculated by the expression $$V \approx \frac{3c\Delta t}{\ln\left(\frac{I_{r1} + I_{r2}}{I_{r2}}\right)}$$

where
c=speed of light, $$I_{r1} = \int_{r0}^{r1} Z(r)dr,$$

$$I_{r2} = \int_{r1}^{r2} Z(r)dr,$$

$r_0$ is the distance at which the field of view of the transmitter and the receiver begin to overlap fully,
$r_1$ is the distance at which the signal has dropped to 10% of the maximum value at the distance $r_0$, and $$r_2 = r_1 - r_0.$$

The integration time of $I_{r1}$ is from $t_0$ to $t_1=t_0+\Delta t$ and the integration time of $I_{r2}$ is from $t_1$ to $t_2=t_1+\Delta t$ where $t_0$, $t_1$, $t_2$ and at are related to $r_0$, $r_1$, $r_2$ and $\Delta r$ as defined in FIG. 2b.

The calculated visibility V is then compared, in a comparison step 407, with a predetermined threshold value in order to give an indication, i.e. a signal, whether or not docking is possible. Specific values for the threshold are determined, e.g., empirically. If the visibility V is greater than the threshold value, an indication is provided in an indication step 409 that the visibility is good and that safe docking is possible. If, on the other hand, the visibility V is less than the threshold value, an indication is provided in an indication step 411 that the visibility is bad and that safe docking is not possible.

Figure 3:
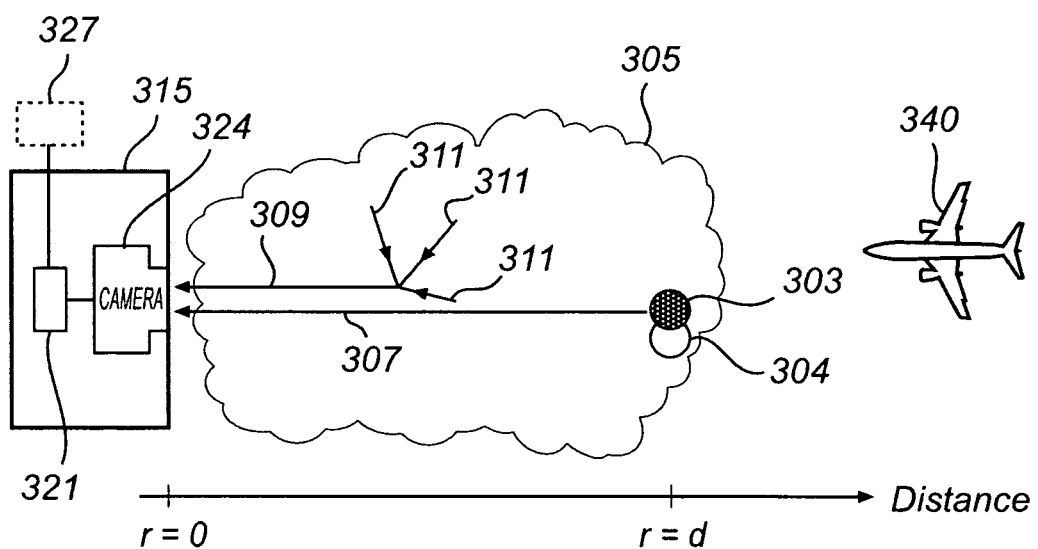
FIG. 3 schematically illustrates a docking system according to a second embodiment of the present invention.

Turning now to FIG. 3, a docking system 315 will be described, which utilizes imaging means in the form of a camera 324. As in the previous embodiment, the docking system 315 is configured to determine, in real-time, distances to approaching aircraft and also configured to indicate whether or not visibility at a docking site is good enough to allow safe docking of an aircraft 340.

The docking system 315 of FIG. 3, which may represent any of the docking systems 115, 117 discussed above in connection with FIG. 1, comprises a control unit 321 connected to the camera 324 and connected to an external control system 327, similar to the situation discussed above in connection with the embodiment of FIG. 2a.

The camera 324 is controlled to record an image of a contrast test object, illustrated by a dark spot 303 and a bright spot 304, located at a distance d from the docking system 315. As the skilled person will realize, the test object 304, 305 may be any predetermined object or marking located at the docking site within the field of view of the docking system, e.g. a part of the painted guiding line 107. Fog 305 is illustrated in FIG. 3 as extending in the atmosphere between the docking system 315 and the approaching aircraft 340.

Figure 5:
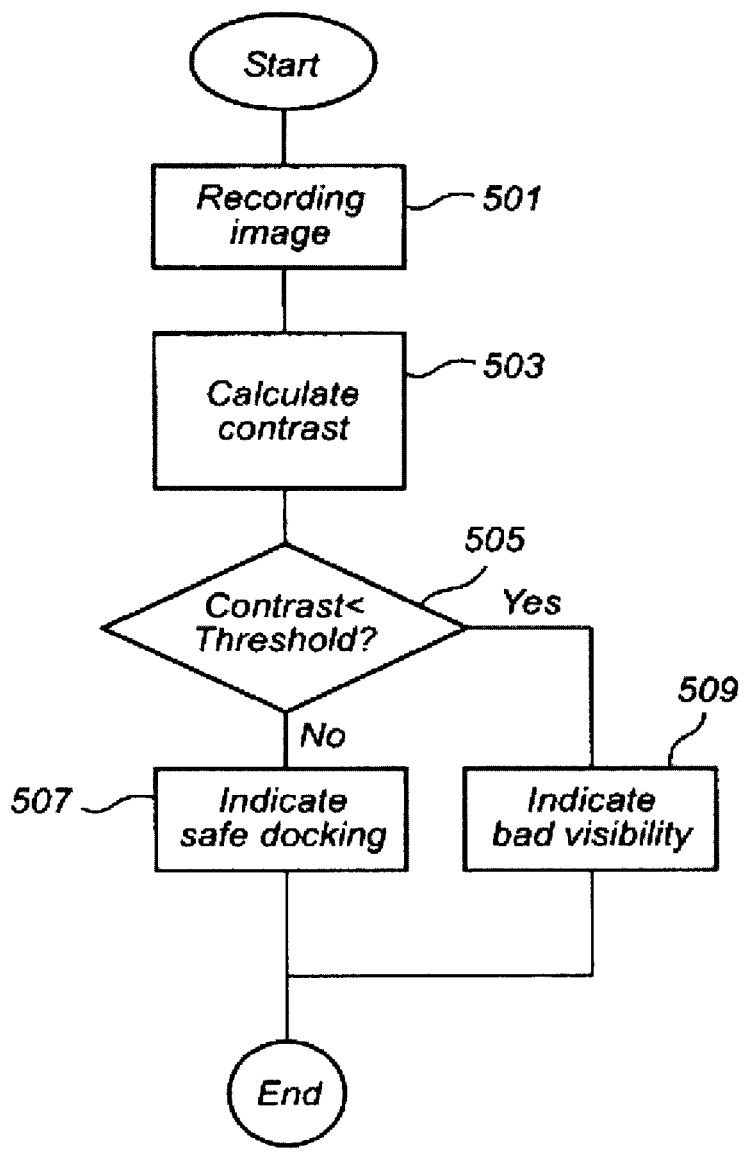

Now follows a description of how the docking system 315 in FIG. 3 operates in order to provide an indication of whether or not safe docking is possible, where the distance determining of the control unit 321 utilizes the camera 324 to record images. In a recorded images a first pixel, denoted i, and a second pixel, denoted j, contain image data of a respective scene point, $P_i$ and $P_j$ that correspond to the respective spots 303, 304 of the calibration object. Reference will be made also to the flow chart in FIG. 5.

After recording an image in a recording step 501 the contrast between the two pixels i and j in the camera image, corresponding to the two scene points $P_i$ and $P_j$ at the same distance d from the camera, is calculated in a calculation step 503. The contrast is then, as will be described below, used as a measure of the performance degradation caused by reduced visibility.

The contrast in the camera image is affected by scattering of light by atmospheric particles in two ways, as shown in FIG. 3. Direct transmission 307 is the attenuated irradiance received by the camera sensor from the scene point 303,304 along the line of sight. Airlight 309 is the total amount of environmental illumination 311 (sunlight, skylight, ground light) reflected into the line of sight by atmospheric particles.

It is known that the following relations apply:

$$E^{(i)} = I_\infty \rho^{(i)} e^{-\beta d} + I_\infty(1 - e^{-\beta d})$$

$$E^{(j)} = I_\infty \rho^{(j)} e^{-\beta d} + I_\infty(1 - e^{-\beta d})$$

where:

$E^{(i)}$ and $E^{(j)}$ is the brightness at the two pixels i and j, respectively.

$I_\infty$ is the environmental illumination intensity, $\rho$ is the normalized radiance of the scene point 303,304, being a function of the scene point reflectance, normalized environmental illumination spectrum and the spectral response of the camera 324, $\beta$ is the backscatter coefficient of the atmosphere in front of the camera 324, and d is the distance between the system 315 and the scene point 303,304.

The observed contrast between $P_i$ and $P_j$ can be defined as $$\frac{E^{(i)} - E^{(j)}}{E^{(i)} + E^{(j)}} = \frac{\rho^{(i)} - \rho^{(j)}}{\rho^{(i)} + \rho^{(j)} + 2(e^{\beta d} - 1)}$$

This shows that the contrast degrades exponentially with the scattering coefficient $\beta$ and the depths of scene points in a situation where the fog 305 is present.

The brightness E of the two pixels are measured and the contrast C(i,j) between the two points is calculated as $$C(i, j) = \frac{E^{(i)} - E^{(j)}}{E^{(i)} + E^{(j)}}$$

The calculated contrast C is then compared, in a comparison step 505, with a predetermined threshold value in order to give an indication, i.e. a signal, whether or not docking is possible. Specific values for the threshold are determined, e.g., empirically. If the contrast C is greater than the threshold value, an indication is provided in an indication step 507 that the visibility is good and that safe docking is possible. If, on the other hand, the contrast C is less than the threshold value, an indication is provided in an indication step 509 that the visibility is bad and that safe docking is not possible.

While preferred embodiments have been set forth in detail above, those skilled in the art who have reviewed the present disclosure will readily appreciate that other embodiments can be realized within the scope of the present invention, which should therefore be construed as limited only by the appended claims.

The invention claimed is:

1. An aircraft docking system configured to be located at a docking site, said system comprising:
   electromagnetic radiation signal reception means for receiving a receiver signal: and
   distance determining means configured to determine, using said electromagnetic radiation signal reception means, at least a distance between the system and an aircraft and where said distance determining means is configured for:
   measuring at least one property of a receiver signal received by said signal reception means, said property being related to the visibility at the docking site,
   comparing said measure of the at least one receiver signal property with a threshold value, and
   depending on said comparison, providing a signal indicative of whether or not the visibility at the docking site is good enough to allow safe docking with the system.

2. The system according to claim 1, configured to measure said at least one receiver signal property at least in terms related to scattering of said electromagnetic radiation.

3. The system according to claim 2, where the distance determining means comprise laser ranging means and where the distance determining means are configured to measure scattering of laser radiation.

4. The system according to claim 2, where the distance determining means comprise radar ranging means and where the distance determining means are configured to measure scattering of radar radiation.

5. The system according to claim 2, where the distance determining means are configured to measure backscattered electromagnetic radiation.

6. The system according to claim 5, where the distance determining means are configured to determine a power distribution of a received signal of the backscattered electromagnetic radiation.

7. The system according to claim 1, where said distance determining means comprise signal reception means comprising imaging means configured to provide two-dimensional images of the docking site and where the distance determining means are configured to measure the at least one property of the receiver signal at least in terms related to a contrast difference between at least two areas within an image.

8. The system according to claim 7, where said imaging means are configured to determine said contrast difference between predetermined locations at the docking site, said predetermined locations corresponding to said least two areas within the image.

9. The system according to claim 8, where said predetermined locations are located substantially at a same distance from the system.

10. The system according to claim 7, where the imaging means are configured to detect electromagnetic radiation in at least a visual wavelength interval.

11. The system according to claim 7, where the imaging means are configured to detect electromagnetic radiation in at least an infrared wavelength interval.

12. A method for controlling aircraft docking in an aircraft docking system located at a docking site, said system comprising distance determining means configured to determine, using electromagnetic radiation signal reception means, at least a distance between the system and an aircraft and wherein said distance determining means perform the steps of:
   measuring at least one property of a receiver signal received by said signal reception means, said property being related to the visibility at the docking site,
   comparing said measure of the at least one receiver signal property with a threshold value, and
   depending on said comparison, providing a signal indicative of whether or not the visibility at the docking site is good enough to allow safe docking with the system.

13. The method according to claim 12, wherein the measuring of at least one receiver signal property comprises measuring at least scattering of said electromagnetic radiation.

14. The method according to claim 13, wherein the measuring involves measuring backscattered electromagnetic radiation.

15. The method according to claim 14, comprising determining a power distribution of the backscattered electromagnetic radiation.

16. The method according to claim 12, where said distance determining means comprise signal reception means comprising imaging means configured to provide two-dimensional images of the docking site and wherein the step of measuring the at least one property of the receiver signal involves measuring at least a contrast difference between at least two areas within an image.

17. The method according to claim 16, wherein said determination of said contrast difference between predetermined locations at the docking site comprises determination of a contrast difference between predetermined locations corresponding to said least two areas within the image.

18. The method according to claim 17, where said predetermined locations are located substantially at a same distance from the system.

19. The method according to claim 12, further comprising controlling operations at an airport at which said docking site is located in accordance with said signal provided in said step of providing.

20. An article of manufacture for controlling aircraft docking in an aircraft docking system located at a docking site, said system comprising distance determining means configured to determine, using electromagnetic radiation signal reception means, at least a distance between the system and an aircraft, wherein said article of manufacture comprises:
- a computer-readable storage medium; and
- code stored on said computer-readable storage medium, said code, when executed on a computer in said system, controlling said distance determining means to perform the steps of:
- measuring at least one property of a receiver signal received by said signal reception means, said property being related to the visibility at the docking site,
- comparing said measure of the at least one receiver signal property with a threshold value, and
- depending on said comparison, providing a signal indicative of whether or not the visibility at the docking site is good enough to allow safe docking with the system.

* * * * *